US008221456B2

(12) United States Patent
Yen

(10) Patent No.: US 8,221,456 B2
(45) Date of Patent: Jul. 17, 2012

(54) VERTICAL REHABILITATION APPLIANCE

(76) Inventor: Sunto Yen, Taipei (TW)

( * ) Notice: Subject to any disclaimer, the term of this patent is extended or adjusted under 35 U.S.C. 154(b) by 616 days.

(21) Appl. No.: 12/434,037

(22) Filed: May 1, 2009

(65) Prior Publication Data

US 2010/0280548 A1 Nov. 4, 2010

(30) Foreign Application Priority Data

Jan. 6, 2009 (TW) ................................ 98200075 U

(51) Int. Cl.
*A61F 5/00* (2006.01)

(52) U.S. Cl. ........... 606/241; 606/237; 602/32; 128/845

(58) Field of Classification Search .................. 606/237, 606/241; 601/23, 24, 33; 602/4, 32, 33, 602/36, 37; 128/845; 482/38, 41, 43, 54, 482/57, 123, 143, 144
See application file for complete search history.

(56) References Cited

U.S. PATENT DOCUMENTS 3,675,646 A * 7/1972 Corcoran ........................ 602/32
4,470,408 A * 9/1984 Gordon ......................... 482/144
4,534,341 A * 8/1985 Bart et al. ..................... 606/241
5,575,765 A * 11/1996 Foster ............................ 602/32
6,971,997 B1 * 12/2005 Ryan et al. ...................... 602/32
2007/0054784 A1 * 3/2007 Wu et al. ......................... 602/32

* cited by examiner

*Primary Examiner* — Quang D Thanh
(74) *Attorney, Agent, or Firm* — Ming Chow; Sinorica, LLC

(57) ABSTRACT

A vertical rehabilitation appliance includes a horizontal frame, vertical frame, moving mechanism, head positioning structure, body positioning structure, and fastening belts. The vertical frame has two first posts coupled to the horizontal frame and formed with holes. The first posts are coupled to a second post. The second post and the horizontal frame are coupled to two third posts. Moving mechanisms are horizontally provided between the first posts and bilaterally provided with positioning devices for engagement with the holes of the first posts. The head positioning structure and the body positioning structure are provided on the moving mechanisms. The fastening belts are provided between the third posts to fix a rehabilitation patient's shoulders and lower limbs in position. Two back-positioned ends of the fastening belts have first connecting elements coupled to a second connecting element so as to pull the rehabilitation patient's back during spine rehabilitation therapy.

9 Claims, 7 Drawing Sheets

VERTICAL REHABILITATION APPLIANCE

FIELD OF THE INVENTION

The present invention relates to a vertical rehabilitation appliance, and more particularly, to an appliance operable in conjunction with a tractor or weight pulling a rehabilitation patient's spine from the back while the patient is standing, so as to perform spine-stretching rehabilitation on the patient efficiently.

BACKGROUND OF THE INVENTION

Owing to technological advancement and economic development, contemporary humankind experience marked changes in lifestyle and workplaces. For instance, in these days, people's sedentary work or study entails maintaining the same posture for a long period of time, and carrying heavy goods while standing is not uncommon among workers. As a result, contemporary people's spine is particularly vulnerable. For example, Bulging disk usually results in compression of the spinal cord especially in the presence the patent's body movement, and in consequence the Bulging disk causes illness to the patient who would have to receive spine-stretching rehabilitation therapy in order to be healed. Spine-stretching rehabilitation therapy can be performed in two ways: spinal stretching performed by machine, and spinal stretching performed by hand. The former is all the range, because the latter requires well-trained know-how and must be followed by screening the patient for special diseases, such as osteoporosis, blood vessel conditions, rheumatoid arthritis, and ankylosing spondylitis.

The related prior art disclosed a conventional method for performing spinal stretching by machine. The method is characterized by: standing a patient up within a vertical frame; resting the patient's axillae on axilla-supporting structures; clamping the patient's waist with waist-supporting structures; and lifting the patient's body slowly by an electrically operating means until the patient's tiptoes do not come into contact with the floor. The operating principle of the method is: stretching the spine by giving a pull at the spine by gravity, that is, by the gravitational pull which originates from the patient's body weight. However, with the patient being hung in the air for a long while, the conventional method for performing spinal stretching by machine causes soreness to the patient's axillae and back muscles, thus deteriorating the efficacy of spine-stretching rehabilitation therapy. Accordingly, the conventional method for performing spinal stretching by machine is not effective in spinal rehabilitation therapy.

SUMMARY OF THE INVENTION

An objective of the present invention is to provide a vertical rehabilitation appliance for standing a rehabilitation patient up and correcting the patient's spinal deformity with a plurality of fastening belts, so as to relieve the pain which might otherwise caused to the patient's axillae and back muscles in the course of spine-stretching rehabilitation therapy.

To achieve the above and other objectives, the present invention provides a vertical rehabilitation appliance, comprising: a horizontal frame, a vertical frame, a moving mechanism, a head positioning structure, a body positioning structure, and at least three fastening belts. The vertical frame has two first posts which are fixed in position to the horizontal frame, corresponding in position to each other, and formed with a plurality of holes aligned and corresponding in position to one another. Top portions of the two first posts are coupled to a second post. The second post and the horizontal frame are coupled to two third posts corresponding in position to each other. A plurality of moving mechanisms are horizontally provided between the two first posts and bilaterally provided with positioning devices for engagement with the holes of the two first posts. The head positioning structure and the body positioning structure are provided on the moving mechanisms. The fastening belts are provided between and coupled to the two third posts to fix a rehabilitation patient's shoulders and lower limbs in position. Two back-positioned ends of the fastening belts have first connecting elements coupled to a second connecting element so as to pull a rehabilitation patient's back while spine rehabilitation therapy is performed thereon.

The present invention is hereunder illustrated with a preferred embodiment in conjunction with the accompanying drawings, so that one skilled in the pertinent art can easily understand the structures, features, and effects of the present invention from the disclosure of the invention.

BRIEF DESCRIPTION OF THE DRAWINGS

The aforesaid objectives, characteristics and advantages of the present invention will be more clearly understood when considered in conjunction with the detailed description of the accompanying embodiment and drawings, in which.

DETAILED DESCRIPTION OF THE INVENTION

Figure 1:
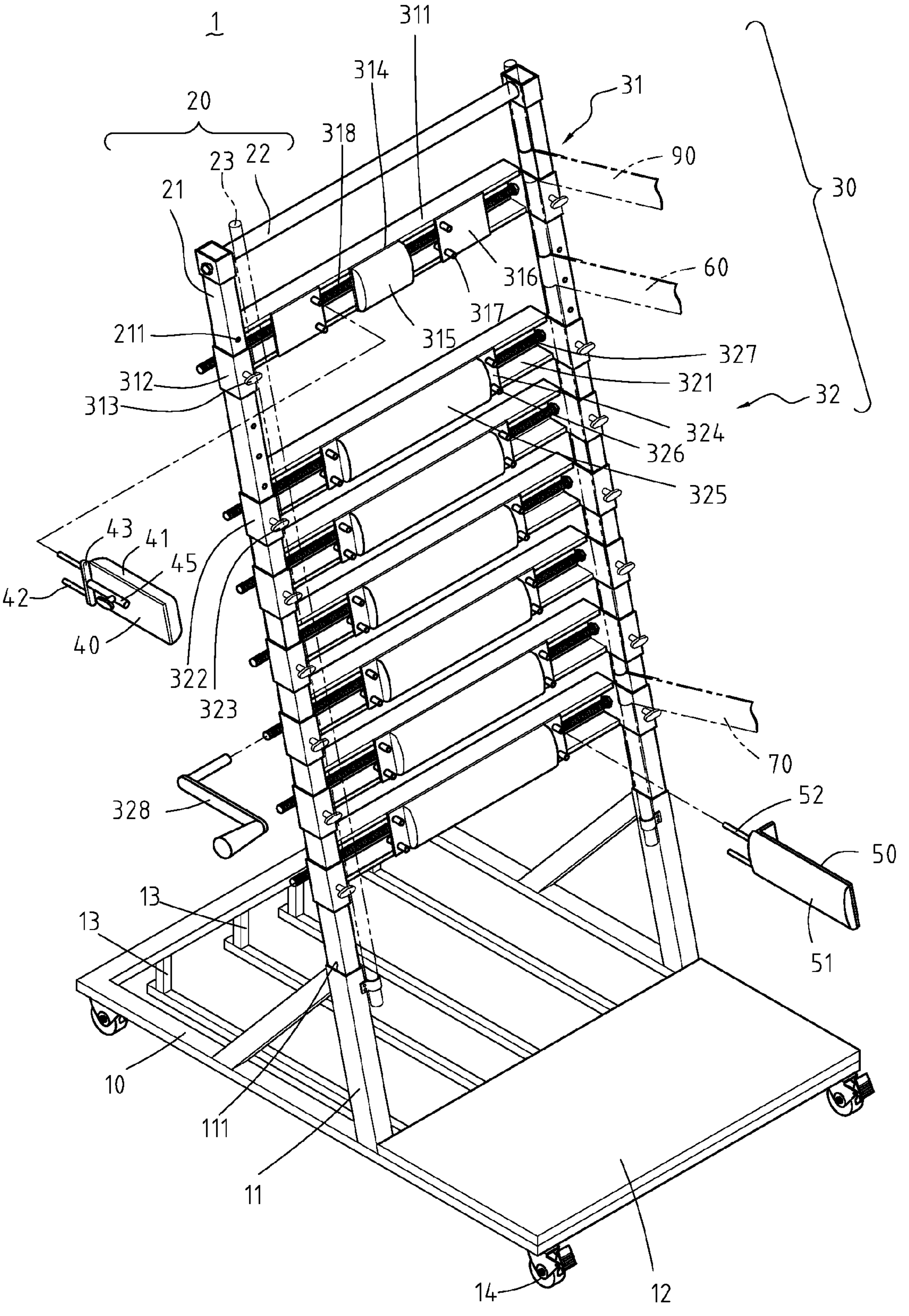
FIG. 1 is a perspective view of a vertical rehabilitation appliance of the present invention.
Figure 2:
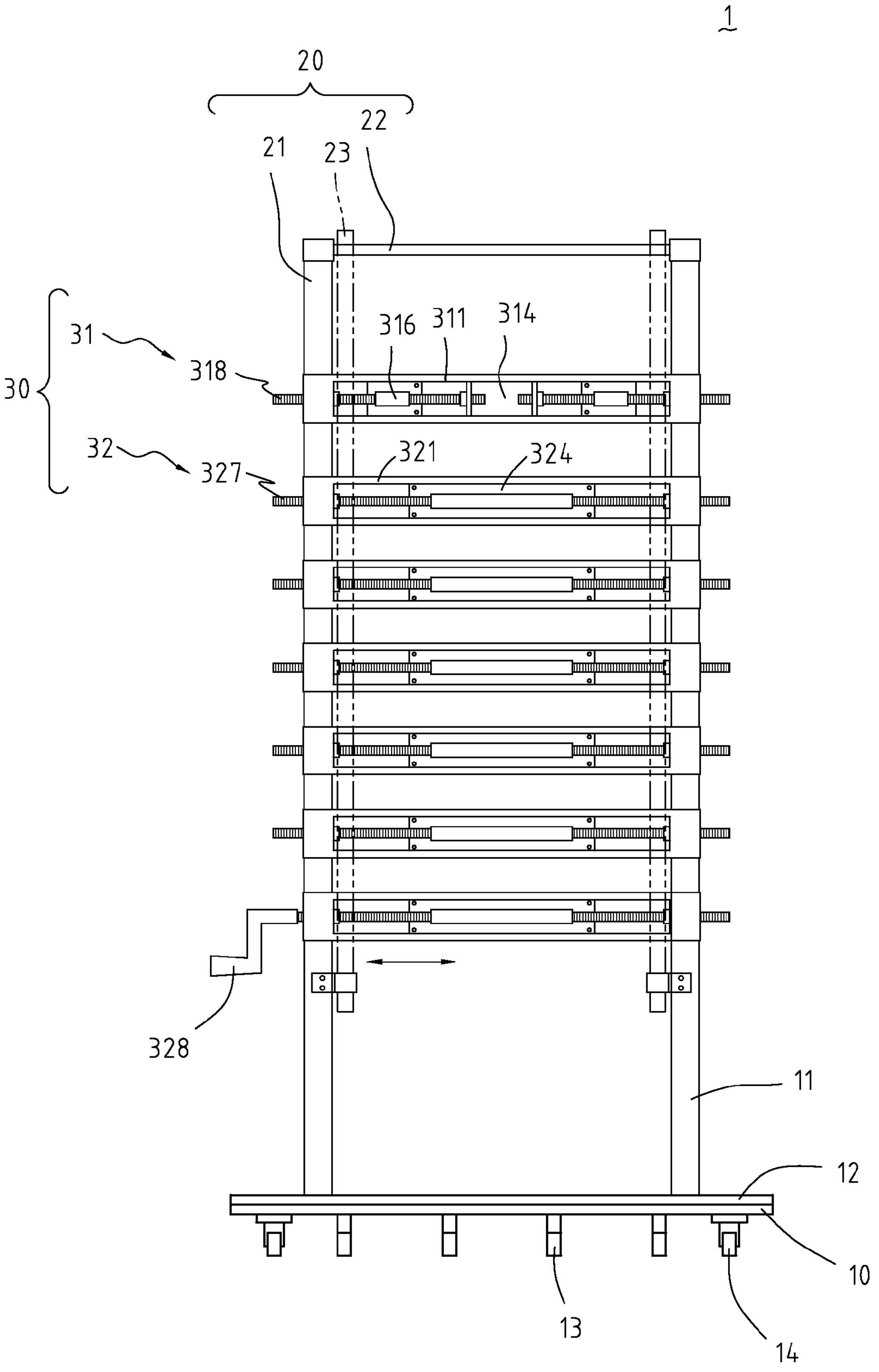
FIG. 2 is a rear elevation view of the vertical rehabilitation appliance of the present invention.
Figure 3:
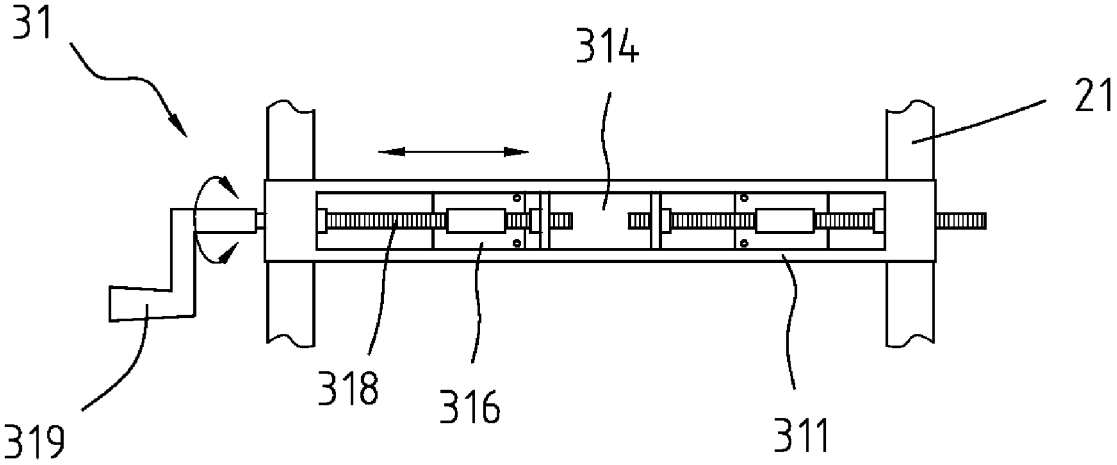
FIG. 3 is a partial rear elevation view illustrating lateral movement of blocks of a first moving mechanism shown in FIG. 2 according to the present invention.

FIG. 1 is a perspective view of a vertical rehabilitation appliance of the present invention. FIG. 2 is a rear elevation view of the vertical rehabilitation appliance of the present invention. FIG. 3 is a partial rear elevation view illustrating lateral movement of blocks of a first moving mechanism shown in FIG. 2 according to the present invention. The present invention provides a vertical rehabilitation appliance 1 essentially comprising: a horizontal frame 10, a vertical frame 20, a plurality of moving mechanisms 30, a head positioning structure 40, and a body positioning structure 50. The above-mentioned is described in detail hereunder.

The vertical frame 20 is bilaterally provided with two first posts 21. The two first posts 21 have a plurality of holes 211 formed therein, respectively, aligned, and corresponding in position to one another. Top portions of the two first posts 21 are coupled to a second post 22.

The horizontal frame 10 is bilaterally provided with two vertical post bases 11. Each of the two vertical post bases 11 has at least a post hole 111 formed therein. The two vertical post bases 11 incline backward and form an included angle greater than 90 degrees with the horizontal frame 10. The two first posts 21 of the vertical frame 20 are inserted into the two post holes 111, respectively. Two third posts 23 are fixed in position between the two vertical post bases 11 and the second post 22 coupled to the top portions of the two first posts 21 of the vertical frame 20. The two third posts 23 are positioned on opposing inner sides of the two first posts 21, respectively. A pedal 12 is provided in front of the two vertical post bases 11. Two positioning frames 13 are provided beneath the horizontal frame 10. Rollers 14 are provided at four corners of the horizontal frame 10.

The moving mechanisms 30 further comprise a first moving mechanism 31 and a plurality of second moving mechanisms 32. The second moving mechanisms 32 are beneath the first moving mechanism 31. There are, say, six said second moving mechanisms 32.

The first moving mechanism 31 has a frame 311. The frame 311 is bilaterally provided with two positioning devices 312. The positioning devices 312 are provided with bolts 313 for engagement with the holes 211 of the two first posts 21 of the vertical frame 20. The frame 311 straddles a head panel 314 and is coupled thereto. The head panel 314 is provided with a soft pad 315. The frame 311 is provided with two blocks 316 which flank the head panel 314. Each of the two blocks 316 has two apertures 317 formed therein. The back of each of the two blocks 316 engages a screw 318. An end portion of the screw 318 is inserted into a handle 319.

The second moving mechanisms 32 has a frame 321. The frame 321 is bilaterally provided with two positioning devices 322. The positioning devices 322 are provided with bolts 323 for engagement with the holes 211 of the two first posts 21 of the vertical frame 20. The frame 321 is provided with a body board 324. The body board 324 is coupled to a soft pad 325. Two apertures 326 which flank the soft pad 325 are formed in the body board 324. The back of the body board 324 engages a screw 327. An end portion of the screw 327 is inserted into a handle 328.

The head positioning structure 40 is provided with a soft pad 41 and two rods 42. The two rods 41 are fixed in position to a long arm 43. The long arm 43 is coupled to a short arm 44. A pipe 45 is pivotally coupled to the short arm 44. The pipe 45 is pivotally coupled to the head positioning structure 40.

The body positioning structure 50 has a soft pad 51 and two rods 52.

A second fastening belt 70 is bilaterally provided with first connecting elements 71.

Referring to FIG. 1, the vertical rehabilitation appliance 1 of the present invention works as follows. With the positioning devices 312 bilaterally provided for the first moving mechanism 31 and the positioning devices 322 bilaterally provided for the second moving mechanisms 32, the first moving mechanism 31 and the second moving mechanisms 32 can move upward or downward along the vertical frame 20 and between the two first posts 21 of the vertical frame 20, so as to identify a level that matches the height of the rehabilitation patient's head and body. Then, the two rods 42 of the head positioning structure 40 are inserted into the apertures 317 of the two blocks 316, respectively, so as for the head positioning structure 40 to be coupled to the two blocks 316 of the first moving mechanism 31, and in consequence the head positioning structure 40 fits lateral sides of the rehabilitation patient's head. Likewise, the two rods 52 of the body positioning structure 50 are inserted into the apertures 326 formed in the body board 324 to flank the soft pad 325, so as for the body positioning structure 50 to be coupled to the body board 324 of the second moving mechanisms 32, and in consequence the body positioning structure 50 fits lateral sides of the rehabilitation patient's body. Alternatively, two said body positioning structures 50 are bilaterally coupled to the body board 324 of the second moving mechanisms 32 in an alternate manner, so as to fit the rehabilitation patient's body shape.

Figure 6:
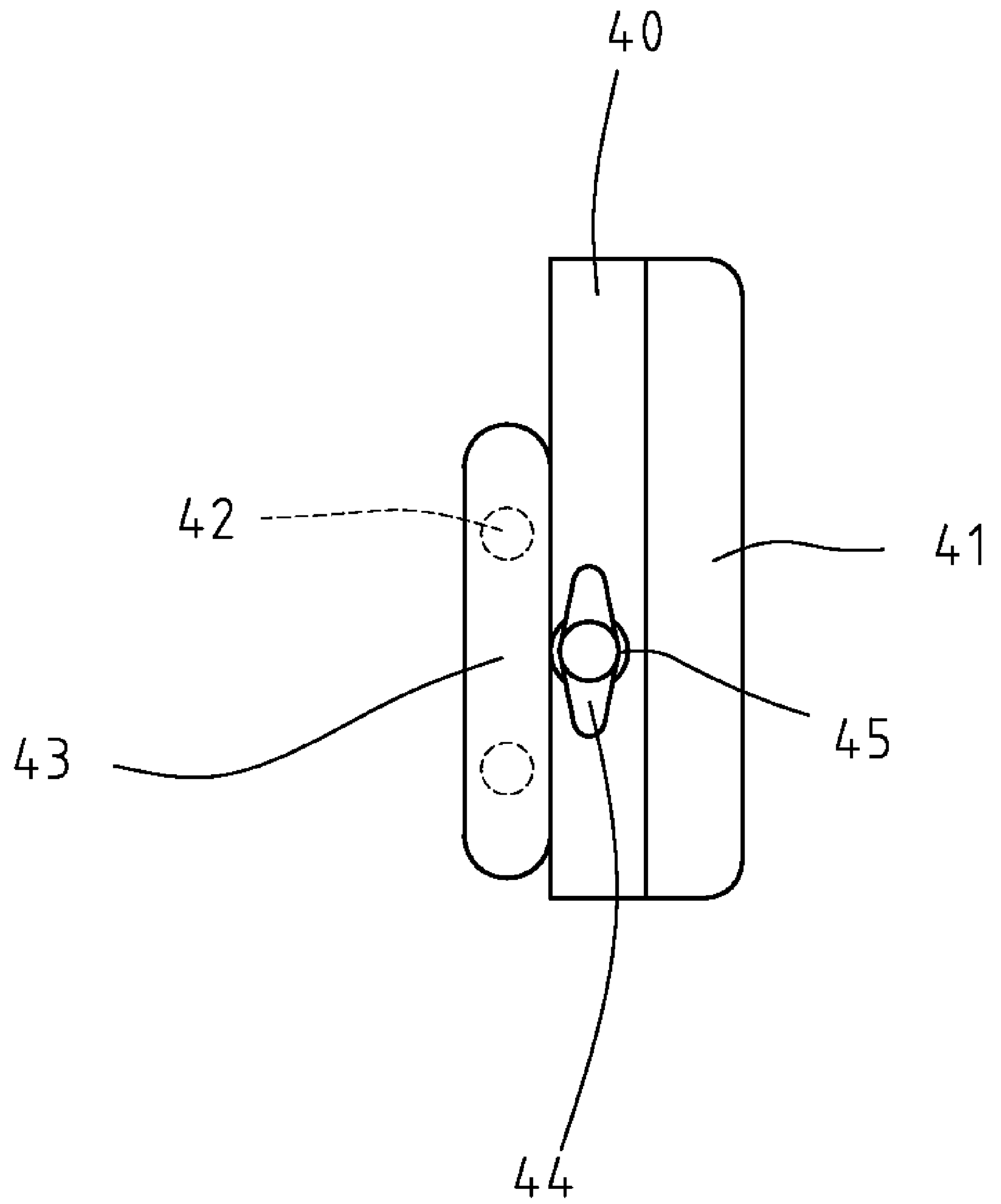
FIG. 6 is a side elevation view of a head positioning structure of the present invention.
Figure 7:
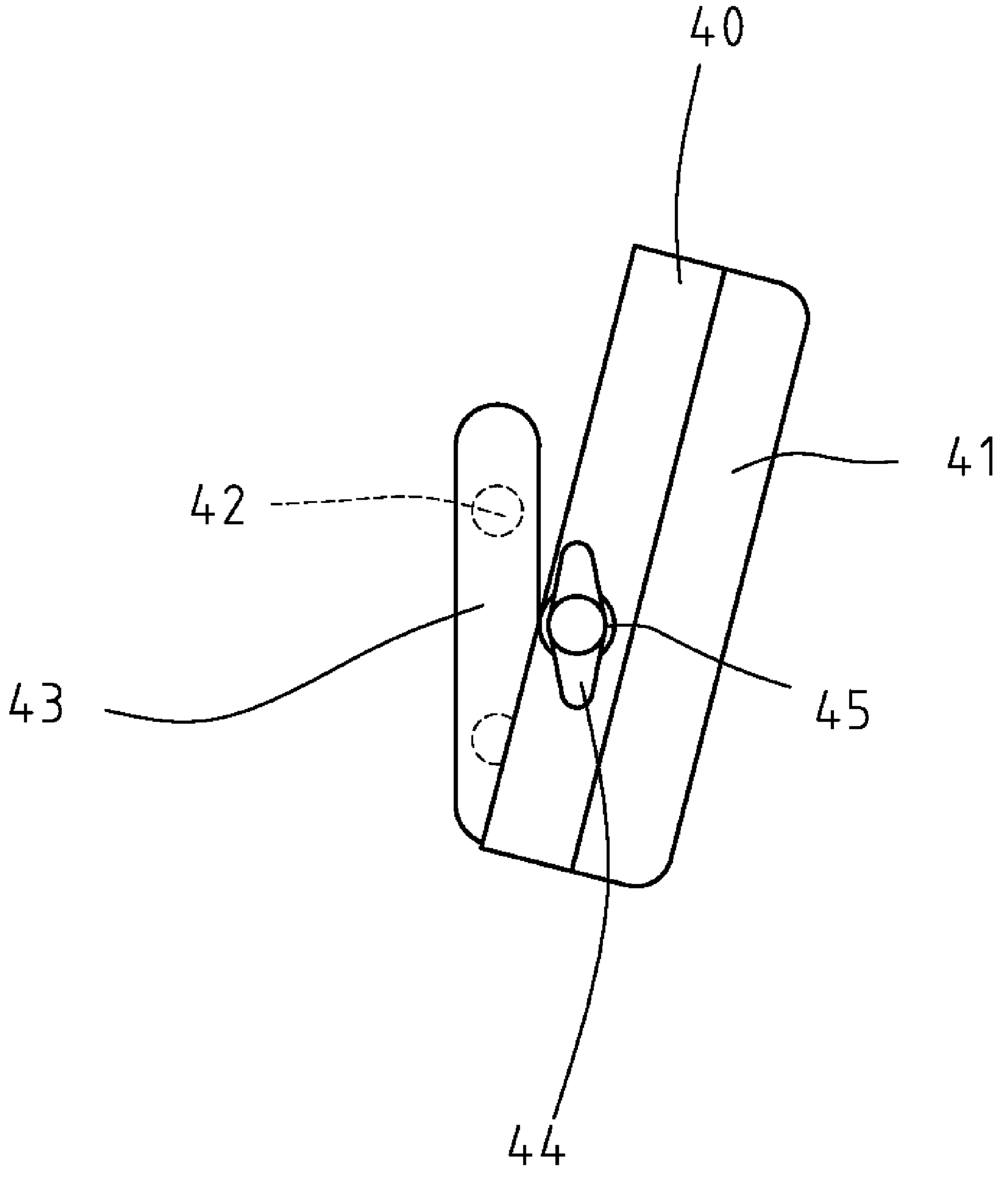
FIG. 7 is a side elevation view illustrating rotation of the head positioning structure shown in FIG. 6 according to the present invention.

Referring to FIG. 6 and FIG. 7, with the short arm 44 and pipe 45 being pivotally coupled to the head positioning structure 40, the inclination of the head positioning structure 40 is adjustable so as to fit the rehabilitation patient's head.

Referring to FIG. 2 and FIG. 3, turning the handle 319 of the first moving mechanism 31 allows the two blocks 316 to be moved sideward by means of the screw 318, so as to identify a distance that matches the width of the rehabilitation patient's head. Likewise, turning the handle 328 of the second moving mechanisms 32 allows the body board 324 to be moved sideward by means of the screw 327, so as to identify a point that matches the standing rehabilitation patient's position.

Figure 4:
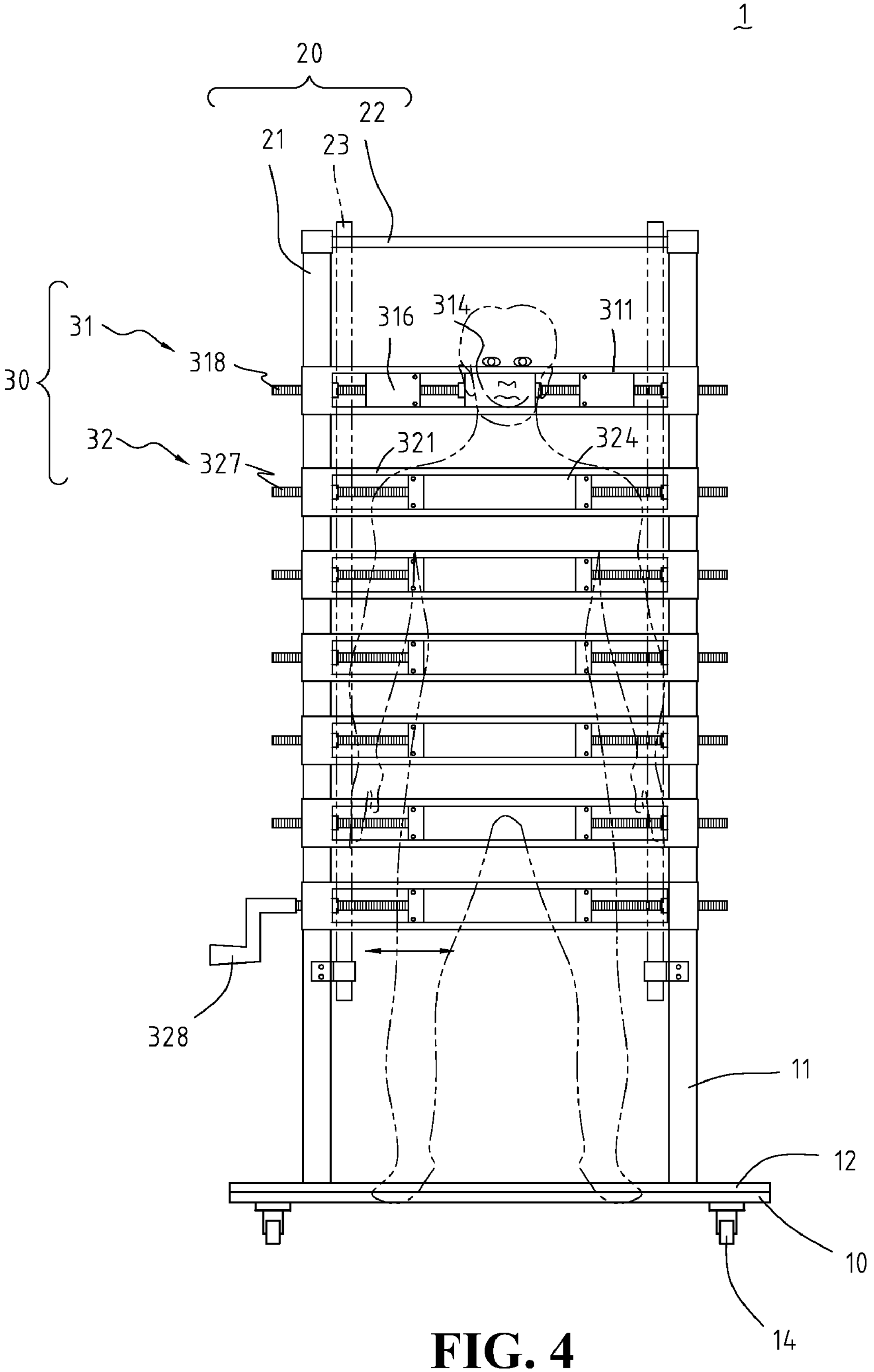
FIG. 4 is a front elevation view showing a rehabilitation patient standing beside the vertical rehabilitation appliance of the present invention.
Figure 5:
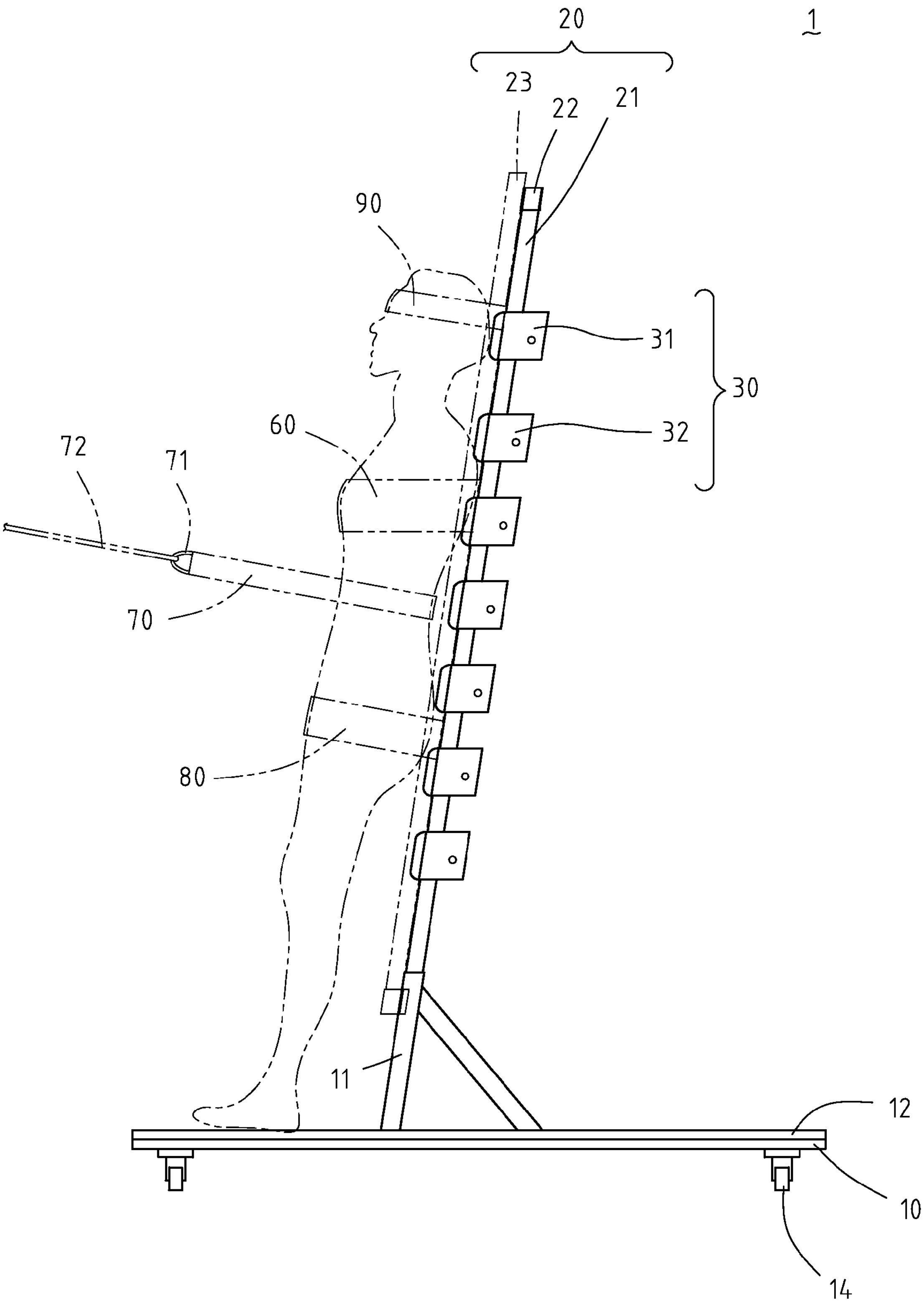
FIG. 5 is a side elevation view showing the rehabilitation patient standing beside the vertical rehabilitation appliance and fixed in position thereto with four fastening belts so as to receive spine-stretching rehabilitation therapy according to the present invention.

Referring to FIG. 4 and FIG. 5, the rehabilitation patient stands on the pedal 12 provided in front of the horizontal frame 10, and rehabilitation patient's head and body lean against the head panel 314 of the first moving mechanism 31 and the body board 324 of the second moving mechanisms 32, respectively. Then, a first fastening belt 60, a third fastening belt 80, and a fourth fastening belt 90 are tied to the two third posts 23 such that the rehabilitation patient's shoulders, lower limbs, and head are fixed in position to the vertical frame 20. Afterward, the second fastening belt 70 passes the rehabilitation patient's waist, and then the first connecting elements 71 bilaterally provided for the second fastening belt 70 are coupled to a second connecting element 72 provided for a cord connected to the tip of a tractor or weight (not shown), so as to give a pull at the rehabilitation patient's back while spine rehabilitation therapy is performed thereon. In a preferred embodiment, the first connecting elements 71 are snap rings, and the second connecting element 72 is a loop, thus allowing the first connecting elements 71 (i.e., the snap rings) to engage the second connecting element 72 (i.e., the loop).

The present invention provides a vertical frame structure to allow a rehabilitation patient to receive rehabilitation therapy while standing at ease, wherein, with a plurality of fastening belts for fixing the rehabilitation patient in position and a tractor for giving a pull at the rehabilitation patient's spine, spine-stretching rehabilitation therapy is efficiently performed on the rehabilitation patient without causing soreness to the rehabilitation patient's muscles. The above-mentioned are the advantages and effect of the present invention.

The above description serves to expound a preferred embodiment of the present invention rather than limit the scope of application of the present invention. Persons skilled in the art should be able to make obvious changes or modification of the present invention without departing from the substantive disclosure of the present invention.

What is claimed is:

1. A vertical rehabilitation appliance, comprising:

a horizontal frame;

a vertical frame having two first posts corresponding in parallel position to each other and fixed to said horizontal frame, each of said two first posts having a plurality of holes formed therein, wherein a plurality of moving mechanisms are horizontally provided between said two first posts and are each bilaterally provided with two positioning devices for engagement with said holes of said two first posts, wherein at least one moving mechanism comprises a first moving mechanism having a frame bilaterally provided with said two positioning devices, said frame straddling a head panel and being coupled thereto, said head panel being provided with a soft pad, said frame being provided with two blocks which flank said head panel, wherein a back of each said two blocks engages a screw, allowing an end portion of said screw to be inserted into a handle, wherein each of said two blocks is coupled to a head positioning structure, wherein each of said blocks has two apertures formed therein, and said head positioning structure is provided with two rods, said two rods being inserted into said two apertures of corresponding said block, wherein said two rods of said head positioning structure are fixed to a long arm, said long arm being coupled to a short arm, said short arm being pivotally coupled to a pipe, said pipe being pivotally coupled to said head positioning structure, such that, with said short arm being pivotally coupled to said pipe, an inclination of said head positioning structure is adjustable;

at least one said head positioning structure provided on said at least one moving mechanism; and at least one body positioning structure provided on said moving mechanisms.

2. The vertical rehabilitation appliance of claim 1, wherein top portions of said two first posts are coupled to a second post, and said second post and said horizontal frame are coupled to two third posts.

3. The vertical rehabilitation appliance of claim 2, further comprising at least three fastening belts provided between and coupled to said two third posts and adapted to fix a rehabilitation patient's shoulders and lower limbs, wherein one of said fastening belts which passing said rehabilitation patient's waist having first connecting elements coupled to a second connecting element so as for said rehabilitation patient's back to be pulled while spine rehabilitation therapy is performed thereon.

4. The vertical rehabilitation appliance of claim 2, wherein said horizontal frame is bilaterally provided with two vertical post bases each having at least a post hole formed therein and inclining backward to form an included angle greater than 90 degrees with said horizontal frame, wherein said two first posts for fixing said vertical frame are inserted into said two post holes, respectively, wherein said two third posts are fixed between said two vertical post bases and said second post of said vertical frame and positioned on opposing inner sides of said two first posts, respectively.

5. The vertical rehabilitation appliance of claim 4, wherein a pedal is provided in front of said two vertical post bases of said horizontal frame.

6. The vertical rehabilitation appliance of claim 1, wherein said moving mechanisms further comprises second moving mechanisms, wherein each of said second moving mechanisms having a frame bilaterally provided with said two positioning devices, said frame being provided with a body board coupled to a soft pad, wherein a back of said body board engages a screw, allowing an end portion of said screw to be inserted into a handle, wherein said body board flanking said soft pad is coupled to said body positioning structure.

7. The vertical rehabilitation appliance of claim 6, wherein two apertures which flank said soft pad are formed in said body board, and said body positioning structure has said soft pad and two rods, said two rods being inserted into said two apertures of said body board.

8. The vertical rehabilitation appliance of claim 3, further comprising a fourth fastening belt provided between and coupled to said two third posts for fixing said rehabilitation patient's head to the vertical rehabilitation of appliance.

9. The vertical rehabilitation appliance of claim 3, wherein said first connecting elements are snap rings, and said second connecting element is a loop, thus allowing said first connecting elements in a form of said snap rings to engage said second connecting element in a form of said loop.

* * * * *